(12) United States Patent
Lee

(10) Patent No.: US 11,987,786 B2
(45) Date of Patent: May 21, 2024

(54) DEVICE FOR REDUCING SIZE OF BIOLOGICAL TISSUE

(71) Applicant: Jun Seok Lee, Busan (KR)

(72) Inventor: Jun Seok Lee, Busan (KR)

(*) Notice: Subject to any disclaimer, the term of this patent is extended or adjusted under 35 U.S.C. 154(b) by 681 days.

(21) Appl. No.: 16/635,621

(22) PCT Filed: Sep. 4, 2018

(86) PCT No.: PCT/KR2018/010278
§ 371 (c)(1),
(2) Date: Jan. 31, 2020

(87) PCT Pub. No.: WO2019/050251
PCT Pub. Date: Mar. 14, 2019

(65) Prior Publication Data
US 2020/0237995 A1    Jul. 30, 2020

(30) Foreign Application Priority Data

Sep. 5, 2017 (KR) .......................... 1020170113331
Aug. 29, 2018 (KR) .......................... 1020180101991

(51) Int. Cl.
A61M 1/34    (2006.01)
A61M 1/00    (2006.01)
C12M 1/33    (2006.01)

(52) U.S. Cl.
CPC .......... C12M 45/02 (2013.01); A61M 1/3406 (2014.02); A61M 1/79 (2021.05); A61M 1/892 (2021.05); A61M 2202/09 (2013.01)

(58) Field of Classification Search
CPC .. A61M 1/3406; A61M 1/79; A61M 2202/09; A61M 1/88; A61M 2202/08;
(Continued)

(56) References Cited

U.S. PATENT DOCUMENTS 3,836,464 A    9/1974  Brookins
3,941,317 A *  3/1976  Kanor .................... C12M 45/02
                                                           422/50
(Continued)

FOREIGN PATENT DOCUMENTS

CN    107107068 A    8/2017
EP       2574663 B1    8/2017
(Continued)

OTHER PUBLICATIONS

European Search Report, dated May 10, 2021 for EP Application No. 18854041.3.
(Continued)

Primary Examiner — Nicholas J. Weiss
Assistant Examiner — Brandon W. Levy
(74) Attorney, Agent, or Firm — George R. McGuire

(57) ABSTRACT

A device for reducing the size of biological tissue according to an embodiment includes a plate, and a thru-hole which penetrates the front and the rear of the plate and is defined by a plurality of edges of the plate, wherein each of the plurality of edges includes a protruding part protruding toward a center part of the thru-hole, and biological tissue may be reduced in size by being scratched and torn by the protruding parts while passing through the thru-hole.

14 Claims, 14 Drawing Sheets

(58) Field of Classification Search
CPC ........ A61M 1/00; A61M 1/02; A61M 1/0259; A61M 1/0272; A61M 1/892; A61M 2205/7545; A61M 1/027; A61B 2017/00792; C12M 45/02; C12M 45/00; C12M 33/14; C12M 25/02; C12M 47/02; C12M 47/04; C12M 47/10; C12M 29/04; G01N 1/286; G01N 2001/2866; G01N 2001/2873; G01N 2001/288; G01N 33/491; G01N 1/04; B02C 18/30; B02C 18/365; B02C 19/20; B02C 18/362; B02C 18/10; B02C 18/36; B02C 2018/367; B02C 19/068; B02C 19/06; C12N 5/0653; B01F 25/452; B01F 25/4521; B01F 25/4522; B01F 25/45221; B01F 25/45231; B01F 25/46; B01F 25/45211; B01F 25/45212; B01F 25/4523; B01F 25/44; B01F 25/40; B01D 69/00; B01D 69/02; B01D 61/147; B26D 3/185; A01J 11/16; A47J 43/25; A47J 43/255
See application file for complete search history.

(56) References Cited

U.S. PATENT DOCUMENTS

| | | | |
|---|---|---|---|
| 5,172,920 A | 12/1992 | Schlenk | |
| 5,626,751 A | 5/1997 | Kikuchi et al. | |
| 5,690,825 A | 11/1997 | Parton | |
| 6,139,757 A | 10/2000 | Ohmura et al. | |
| 10,927,347 B2 | 2/2021 | Pilkington et al. | |
| 2002/0197631 A1 | 12/2002 | Lawrence et al. | |
| 2005/0139704 A1* | 6/2005 | Liao | G01N 1/286 241/169 |
| 2005/0218251 A1* | 10/2005 | Pai | A47J 43/255 241/95 |
| 2011/0264115 A1 | 10/2011 | Asrani et al. | |
| 2013/0327712 A1 | 12/2013 | Delgiacco et al. | |
| 2016/0069781 A1 | 3/2016 | Middlebrook et al. | |
| 2016/0183990 A1 | 6/2016 | Koizumi et al. | |
| 2016/0333305 A1* | 11/2016 | Pilkington | A61M 1/892 |

FOREIGN PATENT DOCUMENTS

| | | | |
|---|---|---|---|
| GB | 863487 | 3/1961 | |
| GB | 863487 A * | 3/1961 | ............ B02C 18/30 |
| JP | 2006187616 A | 7/2006 | |
| JP | 6082816 B2 | 1/2017 | |
| KR | 100748487 B1 | 8/2007 | |
| KR | 1020090020680 A | 2/2009 | |
| KR | 101605849 B1 | 3/2016 | |
| WO | 2011117821 A1 | 9/2011 | |
| WO | 2016/097960 | 6/2016 | |
| WO | WO-2016097960 A2 * | 6/2016 | ............ B02C 18/10 |

OTHER PUBLICATIONS

International Search Report and Written Opinion Form PCT/ISA/210 and PCT/ISA/237, International Application No. PCT/KR2018/010278, pp. 1-7, International Filing Date Sep. 4, 2018, dated Dec. 14, 2018.

* cited by examiner

10

DEVICE FOR REDUCING SIZE OF BIOLOGICAL TISSUE

CROSS REFERENCE TO RELATED APPLICATIONS

This is a U.S. National Stage Application, filed under 35 U.S.C. 371, of International Patent Application No. PCT/KR2018/010278, filed on Sep. 4, 2018, which claims priority to Korean patent application Nos. KR10-2017-0113331, filed Sep. 5, 2017, and KR 10-2018-0101991, filed Aug. 29, 2018, the contents of each of which are incorporated herein by reference in their entireties.

TECHNICAL FIELD

One or more example embodiments relate to a device for reducing a size of biological tissue.

BACKGROUND ART

Fat tissue, which is a kind of biological tissue, is obtained from a subject such as a person or an animal by suction or incision. Since the obtained fat tissue may be large in size and include a large amount of fibrous material, it is difficult to implant the fat tissue into the subject using a fine needle. Accordingly, a device for reducing a size of biological tissue such as the large fat tissue have been developed. For example, U.S. Pat. No. 6,139,757 discloses a method of separating cells from blood using a variable porosity filter.

DISCLOSURE OF INVENTION

Technical Goals

An aspect provides a device for reducing a size of a biological tissue by scratching or tearing the biological tissue.

Another aspect provides a device for gradually reducing a size of a biological tissue. Technical solutions According to an aspect, there is provided a device for reducing a size of a biological tissue, the device including a plate and a through hole defined by a plurality of edges of the plate and penetrating a front and a rear of the plate, wherein each of the plurality of edges includes a protrusion that protrudes toward a central portion of the through hole, and while a biological tissue passes through the through hole, the biological tissue is scratched and torn by the protrusion so that a size of the biological tissue is reduced.

A width of the protrusion may decrease toward the central portion of the through hole such that a tip is formed.

Each of the plurality of edges may include linear portions formed on both sides based on the protrusion. In other words, the protrusion may be formed in a central portion of the edge.

The device may further include a first group of protrusions protruding in a first direction based on the plate while forming an angle with respect to the plate, and a second group of protrusions protruding in a second direction differing from the first direction based on the plate while forming an angle with respect to the plate. In other words, the first group of protrusions and the second group of protrusions may be provided in various ways. For example, the first group of protrusions may appear consecutively along a portion of the plurality of edges and the second group of protrusions may appear consecutively along a remaining portion of the plurality of edges.

The first group of protrusions and the second group of protrusions may alternate in different directions along the plurality of edges.

Extension lines of the first group of protrusions do not meet and are not parallel to extension lines of the second group of protrusions. In other words, an extension line of the first direction and an extension line of the second direction may be at skew positions.

The device may further include an extension portion configured to extend from each of the plurality of edges toward the central portion of the through hole, and a tip formed at an end of the extension portion and configured to scratch and tear the biological tissue.

The device may further include an additional extension portion formed on a side opposite to the extension portion based on the tip and configured to extend toward the central portion of the through hole.

A protruding direction of the protrusion may not be parallel to a moving direction of the biological tissue passing through the through hole.

According to another aspect, there is provided a device for reducing a size of a biological tissue, the device including: a first screen including a first plate, a first through hole defined by a plurality of first edges of the first plate and penetrating a front and a rear of the first plate, and a first protrusion that protrudes toward a central portion of the first through hole; and a second screen including a second plate laminated to the first plate, a second through hole defined by a plurality of second edges of the second plate and penetrating a front and a rear of the second plate, and a second protrusion that protrudes toward a central portion of the second through hole, wherein the first through hole overlaps the second through hole and is larger in size than the second through hole.

Protruding directions of the first protrusion and the second protrusion may not be parallel to a moving direction of a biological tissue sequentially passing through the first through hole and the second through hole, and may be the same as or intersect with the moving direction.

Effects of Invention

According to example embodiments, it is possible to provide a device for reducing a size of a biological tissue by scratching or tearing the biological tissue.

According to example embodiments, it is possible to provide a device for gradually reducing a size of a biological tissue.

The effects of obtainable from the present disclosure are non-limited by the above-mentioned effects. And, other unmentioned effects can be clearly understood from the following description by those having ordinary skill in the technical field to which the present disclosure pertains.

BEST MODE FOR CARRYING OUT THE INVENTION

Figure 1:
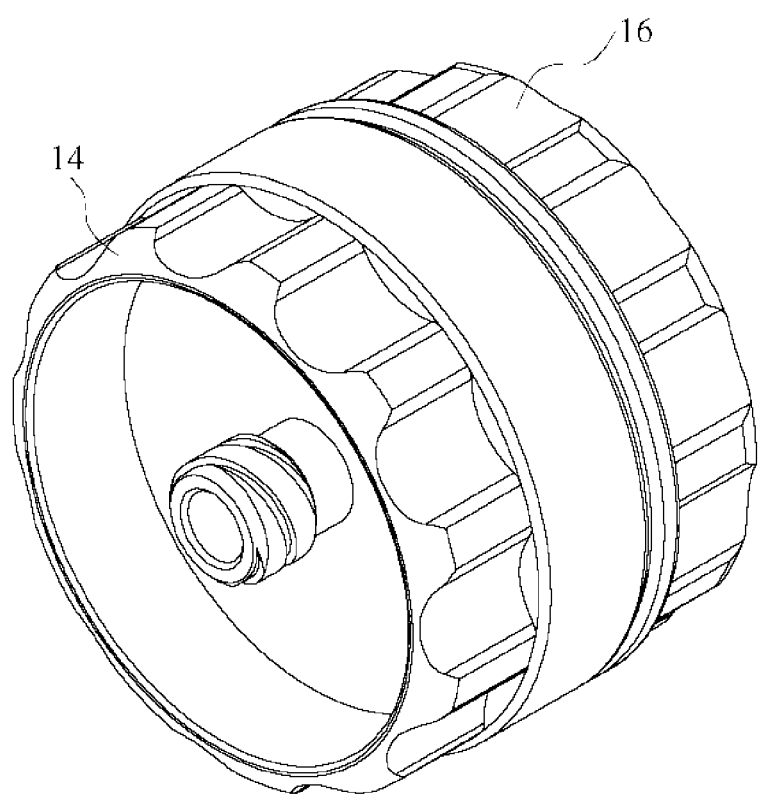
FIG. 1 is a perspective view illustrating a device for reducing a size of a biological tissue according to an example embodiment.

Hereinafter, example embodiments will be described in detail with reference to the accompanying drawings. It should be understood, however, that there is no intent to limit this disclosure to the particular example embodiments disclosed. On the contrary, example embodiments are to cover all modifications, equivalents, and alternatives falling within the scope of the example embodiments.

Although terms such as "first," "second," "A", "B", "a", and "b" may be used herein to describe various members, components, regions, layers, or sections, these members, components, regions, layers, or sections are not to be limited by these terms. Throughout the specification, when an element, such as a layer, region, or substrate, is described as being "on," "connected to," or "coupled to" another element, it may be directly "on," "connected to," or "coupled to" the other element, or there may be one or more other elements intervening therebetween.

Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

Figure 2:
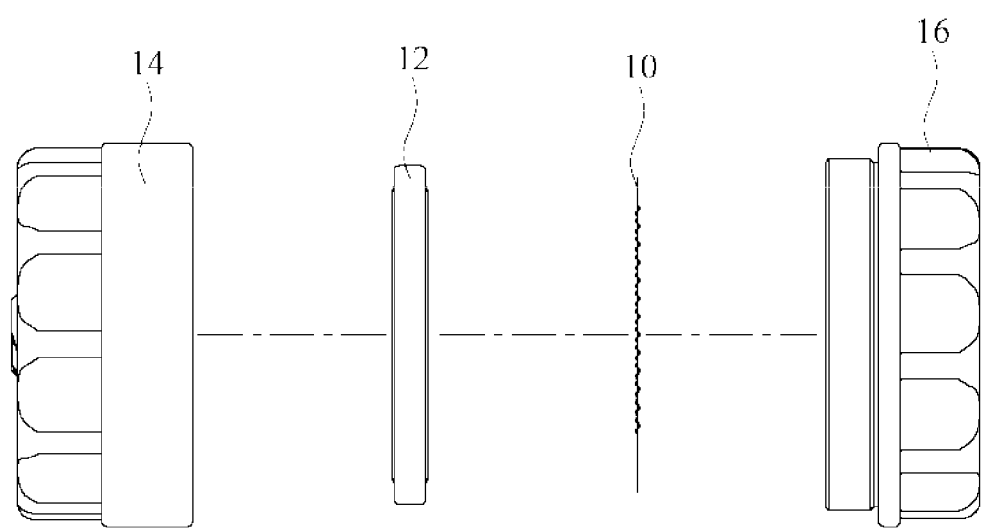
FIG. 2 is an exploded side view illustrating a device for reducing a size of a biological tissue according to an example embodiment.
Figure 3:
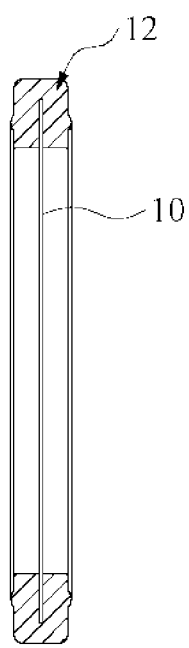
FIG. 3 is a cross-sectional view illustrating a device for reducing a size of a biological tissue according to an example embodiment.

FIG. 1 is a perspective view illustrating a device for reducing a size of a biological tissue according to an example embodiment, FIG. 2 is an exploded side view illustrating a device for reducing a size of a biological tissue according to an example embodiment, and FIG. 3 is a cross-sectional view illustrating a device for reducing a size of a biological tissue according to an example embodiment.

Referring to FIGS. 1 and 2, a device 1 for reducing a size of a biological tissue may be configured to miniaturize a biological tissue and maximize a contact with a biological tissue to acquire a biological tissue in a desired size The biological tissue may include, for example, an adipose tissue. The biological tissue may be obtained from a living body of a subject such as a human being, an animal, or the like, by suction or incision.

The device 1 may include a screen 10, a sealing member 12, a front cover 14, and a rear cover 16.

The screen 10 may be configured to reduce a size of a biological tissue. For example, the screen 10 may have a disk shape. When a lump-shaped biological tissue passes through the screen 10, the screen 10 may scratch or tear the biological tissue.

The sealing member 12 may cover an exterior of the screen 10. The sealing member 12 may form a seal between the screen 10 and each of the front cover 14 and the rear cover 16. The sealing member 12 may have a ring shape. For example, the sealing member 12 may be formed with a rubber material.

The front cover 14 and the rear cover 16 may accept the screen 10 and the sealing member 12, respectively. The front cover 14 and the rear cover 16 may be coupled to each other. For example, the front cover 14 and the rear cover 16 may be rotationally coupled.

The front cover 14 and the rear cover 16 may respectively include an inlet port and an outlet port through which the biological tissue flows. A passage connecting the inlet port and the outlet port may be between the front cover 14 and the rear cover 16. The biological tissue or a mass thereof may flow inside the front cover 14 via the inlet port, pass the screen 10 along the passage, and then flow from inside to outside the rear cover 16 via the outlet port.

Figure 4:
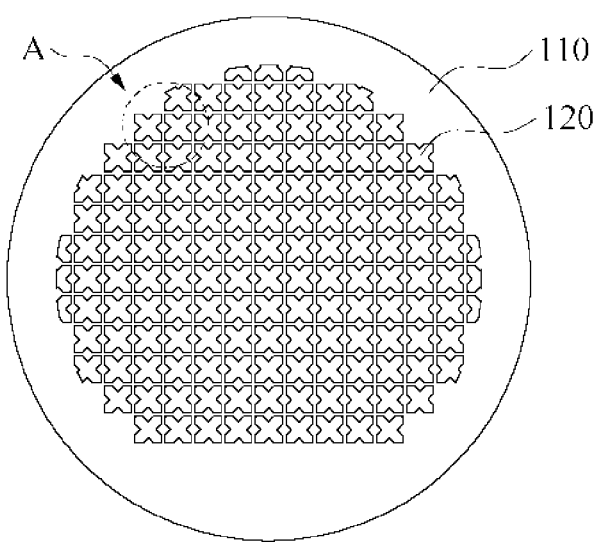
FIG. 4 is a top view illustrating a screen according to an example embodiment.

FIG. 4 is a top view illustrating a screen according to an example embodiment.

Referring to FIG. 4, the screen 10 may include a plate 110 and at least one through hole 120.

The plate 110 may have a disk shape. For example, the plate 110 may have a circular shape. The plate 110 may be formed of a material suitable for preventing a contamination of a biological tissue.

The through hole 120 may miniaturize the biological tissue and maximize a contact with the biological tissue. The through hole 120 may penetrate a front and a rear of the plate 110 and be defined by a plurality of edges of the plate 110. The plurality of edges of the plate 110 that define the through hole 120 may have irregular sizes.

The plate 110 may be plate-molded overall so that a position at which the through hole 120 is formed in the plate 110 is not changed or a shape of the through hole 120 is not deformed by an external force.

Figure 5:
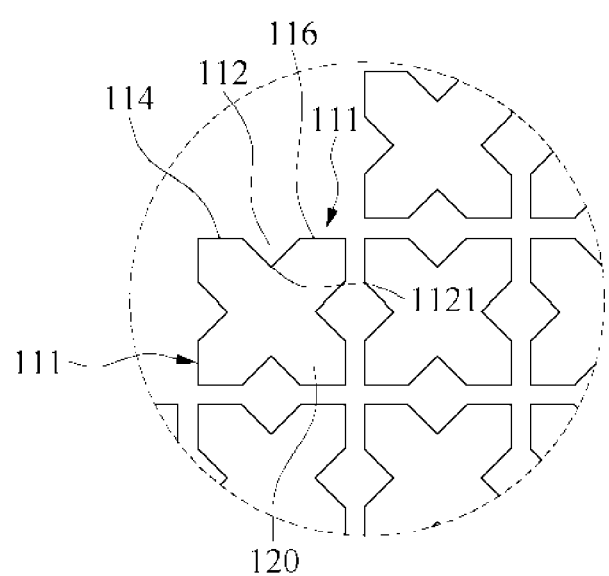
FIG. 5 is an enlarged view illustrating an example of a part A of FIG. 4.

FIG. 5 is an enlarged view illustrating an example of a part A of FIG. 4.

Referring to FIG. 5, a plurality of edges 111 that define the through hole 120 may define the through hole 120 such that the through hole 120 substantially has a quadrangular shape.

Each of the plurality of edges 111 may include a protrusion 112. The protrusion 112 may protrude toward a central portion of the through hole 120. While a biological tissue passes through the through hole 120, the protrusion 112 may scratch or tear the biological tissue. Among constituent components of the biological tissue, a fiber which is greater in size than the through hole 120 may not pass through the through hole 120.

A protruding direction of the protrusion 112 may not be parallel to a moving direction of the biological tissue passing through the through hole 120. For example, the protruding direction of the protrusion 112 may be parallel to a tangential direction of the plate 110 or may be at a set angle with respect to the tangential direction of the plate 110. Here, an angle between the protrusion 112 and the plate 110 may be set as an acute angle, an obtuse angle, or a reflex angle.

A width of the protrusion 112 may decrease toward the central portion of the through hole 120, so that a tip 1121 is formed. For example, the protrusion 112 may have a triangular shape.

The plurality of edges 111 may include linear portions 114 and 116 formed on both sides based on the protrusion 112. In other words, the protrusion 112 may be located in a central portion of the edge 111. For example, the linear portions 114 and 116 may have the same length such that the protrusion 112 is at a center of the edge 111. In this example, the protrusion 112 of the edge 111 and a protrusion of an edge facing the edge 111 may face each other toward the central portion of the through hole 120. Although not shown, the linear portions 114 and 116 may also have different lengths. Lengths of the linear portions 114 and 116 may be adjusted based on a size of the protrusion 112.

As such, due to an irregular shape of the through hole 120 defined by the plurality of edges 111, sharp cross-sections of the plurality of edges 111, and the like, a pressure may be applied to the biological tissue passing through the through hole 120 so that the lump-shaped biological tissue may be torn or scratched.

Figure 6:
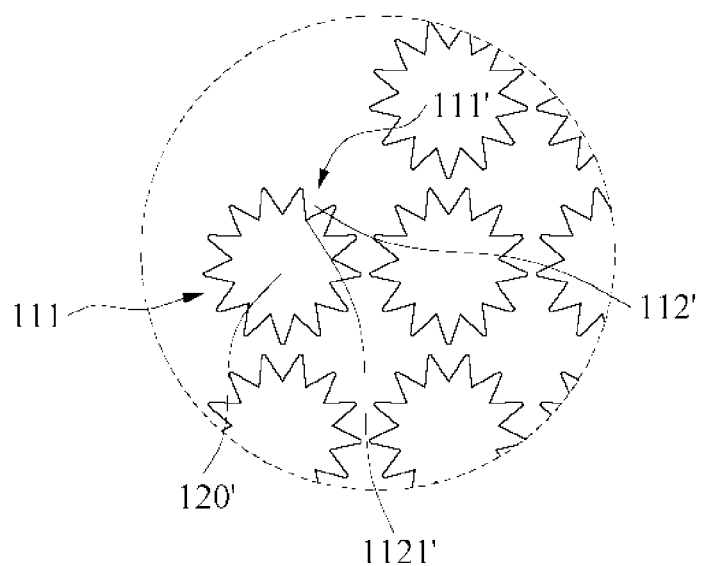
FIG. 6 is an enlarged view illustrating another example of the part A of FIG. 4.

FIG. 6 is an enlarged view illustrating another example of the part A of FIG. 4.

Referring to FIG. 6, a plurality of edges 111' that define the through hole 120 may define the through hole 120 such that the through hole 120 substantially has a polygonal shape having at least four corners. The plurality of edges 111' may include a protrusion 112' that protrudes toward the central portion of the through hole 120. A width of the protrusion 112' may decrease toward the central portion of the through hole 120 so that a tip 1121 is formed.

In the example embodiment, the plurality of edges 111' may not have linear portions formed on both sides based on the protrusion 112' or may have linear portions with lengths relatively small when compared to a size of the protrusion 112'. In other words, a plurality of protrusions 112' may be adjacent to one another along the plurality of edges 111'.

Figure 7:
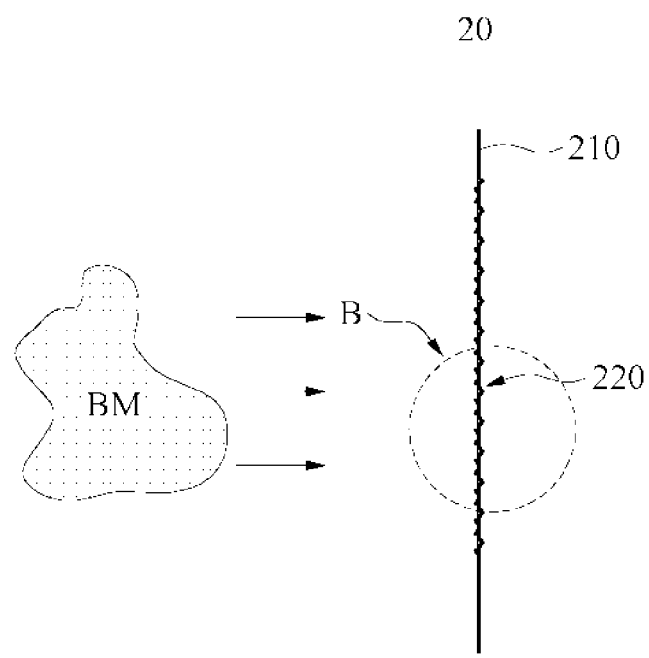
FIG. 7 is a side view illustrating a screen according to an example embodiment.
Figure 8:
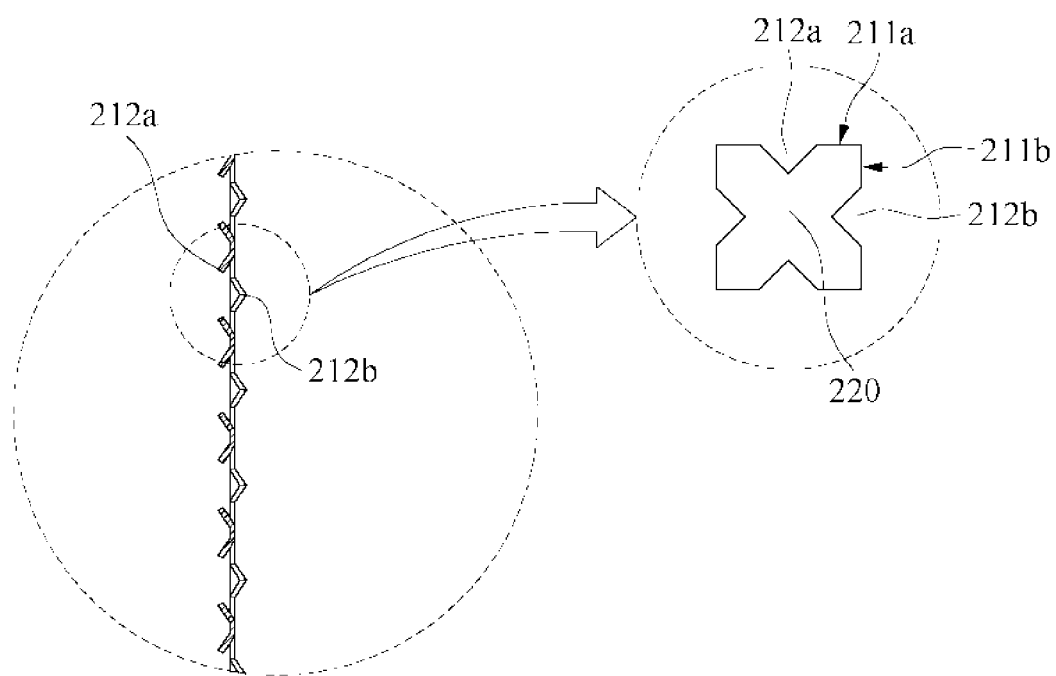
FIG. 8 is an enlarged view illustrating an example of a part B of FIG. 7.

FIG. 7 is a side view illustrating a screen according to an example embodiment, and FIG. 8 is an enlarged view illustrating an example of a part B of FIG. 7.

Referring to FIGS. 7 and 8, a screen 20 may include a plate 210 and a through hole 220. In the example embodiment, protrusions 212a and 212b of a plurality of edges 211a and 211b of the plate 210 may be at a set angle with respect to a tangential direction of the plate 210. A moving direction of a lump-shaped biological tissue BM passing through the through hole 220 from a front of the screen 20 to a rear of the screen 20 may nor parallel to protruding directions of the protrusions 212a and 212b. The protrusions 212a and 212b may reduce a size of the biological tissue BM by scratching or tearing the biological tissue BM instead of slicing the biological tissue BM.

The plurality of edges 211a and 211b may include the protrusions 212a and 212b having at least one directivity relative to the tangential direction of the plate 210. In other words, the plurality of protrusions 212a, 212b may be classified into a plurality of groups. For example, the plurality of protrusions 212a, 212b may be classified into a first group of protrusions that protrude in a first direction based on the plate 210 while forming an angle with respect to the plate 210 and a second group of protrusions that protrude in a second direction based on the plate 210 while forming an angle with respect to the plate 210.

Here, the first direction may be different from the second direction. The first direction differing from the second direction may indicate that the first direction is not parallel to the second direction. For example, referring to FIG. 8, the protrusion 212a of the first direction may protrude to a left side of the plate 210 and the protrusion 212b of the second direction may protrude to a right side of the plate 210.

In one example, the protrusion 212a of the first group and the protrusion 212b of the second group may be adjacent to each other. In a preferred example, the protrusion 212a of the first group and the protrusion 212b of the second group may be alternated with each other.

Although not shown, the plurality of protrusions 212a in the first group and the plurality of protrusions 212b in the second group may be grouped and adjacent in each of the groups. In this case, the plurality of protrusions 212a in the first group may be sequentially formed on a portion of the plurality of edges 211a and 211b, and the plurality of protrusions 212b in the second group may be sequentially formed on a remaining portion of the plurality of edges 211a and 211b.

As such, the plurality of protrusions 212a in the first group and the plurality of protrusions 212b in the second group may be arranged in various ways.

In an example embodiment, an extension line of the protrusion 212a in the first group may not meet and not be parallel to an extension line of the protrusion 212b in the second group. In other words, the extension line of the protrusion 212a in the first group and the extension line of the protrusion 212b in the second group may be at skew positions in a three-dimensional (3D) space. For example, a vertex at which the edge 211a including the protrusion 212a of the first group meets the edge 211b including the protrusion 212b of the second group may be set to be an origin. In addition, the first direction in which the protrusion 212a of the first group protrudes may be set to be an x axis, the second direction in which the protrusion 212b of the second group protrudes may be set to be an y axis, and an outer product of the first direction and the second direction may be set to be a z axis. In this example, a vector from the edge 212a including the protrusion 212a of the first group to a tip of the edge 212a may be (1, 0, −1), and a vector from the edge 212b including the protrusion 212b of the second group to a tip of the edge 212b may be (−1, 0, 1).

Figure 9:
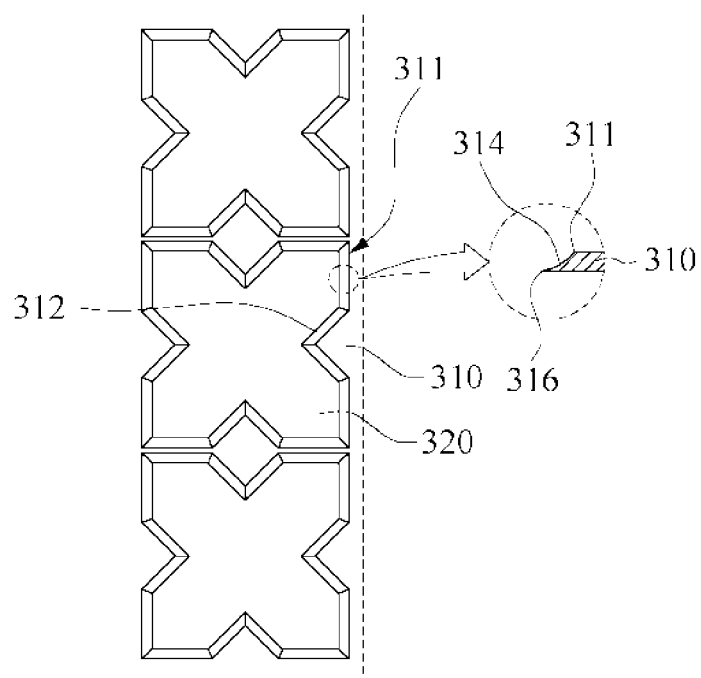
FIG. 9 is a view illustrating an example of a screen and a portion of the screen with an enlarged cross section according to an example embodiment.

FIG. 9 is a view illustrating an example of a screen and a portion of the screen with an enlarged cross section according to an example embodiment.

Referring to FIG. 9, a screen 30 may include a plate 310 and a through hole 320. In the example embodiment, a sharp cross section may be formed over a plurality of edges 311 of the plate 310 that define the through hole 320. For example, the screen 30 may include an extension portion that extends from each of the plurality of edges toward a central portion of the through hole 320 and a tip 316 formed at an end of the extension portion 314 to scratch and tear a biological tissue.

The extension portion 314 may have any suitable shape. In one example, the extension portion 314 may be formed to be inclined based on a plane of the plate 310. In another example, the extension portion 314 may be outwardly curved based on the plate 310.

Figure 10:
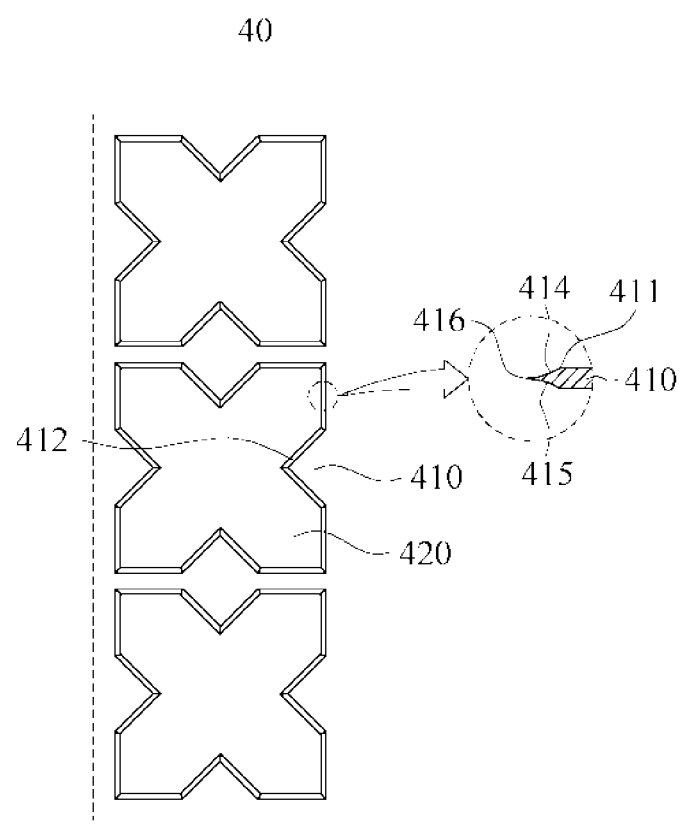
FIG. 10 is a view illustrating another example of a screen and a portion of the screen with an enlarged cross section according to an example embodiment.

FIG. 10 is a view illustrating another example of a screen and a portion of the screen with an enlarged cross section according to an example embodiment.

Referring to FIG. 10, a screen 40 may include a plate 410 and a through hole 420. In this example embodiment, a plurality of edges 411 that defines the through hole 420 may have a plurality of extension portions 414 and 415 formed on both sides based on a tip 416. In one example, the plurality of extension portions 414 and 415 may be formed on the plurality of edges 411 to be inclined at set angles with respect to the plate 410. In a preferred example, the angles at which the plurality of extension portions 414 and 415 are inclined relative to the plate 410 may be substantially the same.

In an additional example embodiment, the plurality of extension portions 414 and 415 may be outwardly curved based on the plate 310. In this case, the plurality of extension portions 414 and 415 may be curved in different directions. For example, curvature radiuses of the plurality of extension portions 414 and 415 may be substantially the same such that the tip 416 is located at a center between the plurality of extension portions 414 and 415.

Figure 11:
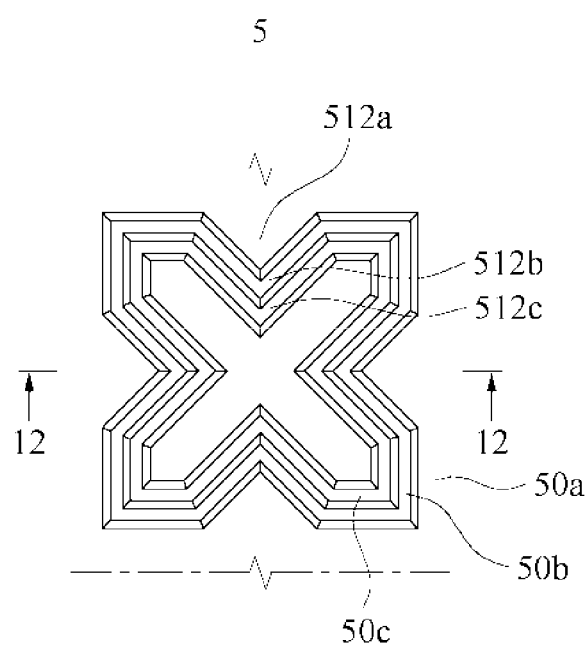
FIG. 11 is a top view illustrating an example of a plurality of laminated screens according to an example embodiment.
Figure 12:
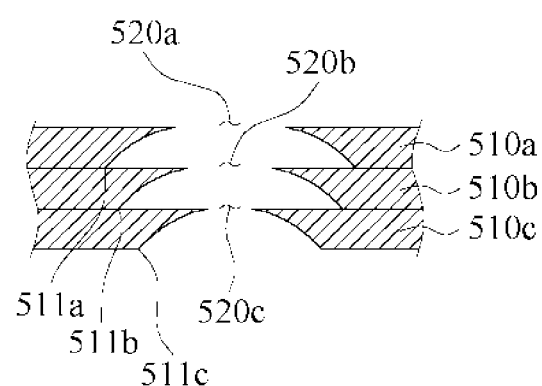
FIG. 12 is a cross-sectional view taken along a line 12-12 of FIG. 11.

FIG. 11 is a top view illustrating an example of a plurality of laminated screens according to an example embodiment, and FIG. 12 is a cross-sectional view taken along a line 12-12 of FIG. 11.

Referring to FIGS. 11 and 12, a device 5 for reducing a size of a biological tissue may include a plurality of screens 50a, 50b, and 50c laminated in sequence. The plurality of screens 50a, 50b, and 50c may respectively include plates 510a, 510b, and 510c and through holes 520a, 520b, and 520c defined by a plurality of edges 511a, a plurality of edges 511b, and a plurality of edges 511c. The plurality of screens 50a, 50b, and 50c may include protrusions 512a, 512b, and 512c protruding toward through holes 520a, 520b, and 520c. As described with reference to FIG. 9, the plurality of edges 511a, 511b, and 511c may each have an extension portion and a tip.

In the example embodiment, the through holes 520a, 520b, and 520c of the plurality of screens 50a, 50b, and 50c laminated in sequence (from top to bottom as shown in FIG. 12) may overlap one another in a direction in which sizes thereof decrease. Through this, a biological tissue passing through the plurality of screens 50a, 50b, and 50c may be gradually miniaturized while receiving a pressure applied due to a sharp cross section formed over the plurality of edges 511a, 511b, and 511c and/or shapes of the protrusions 512a, 512b, and 512c.

Figure 13:
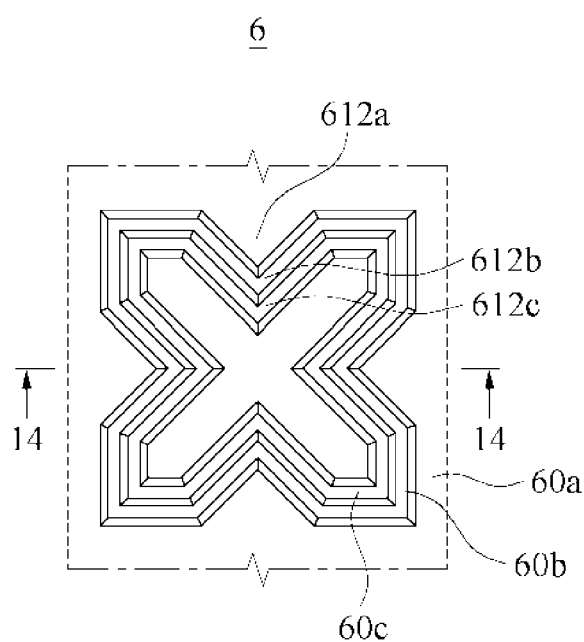
FIG. 13 is a top view illustrating another example of a plurality of laminated screens according to an example embodiment.
Figure 14:
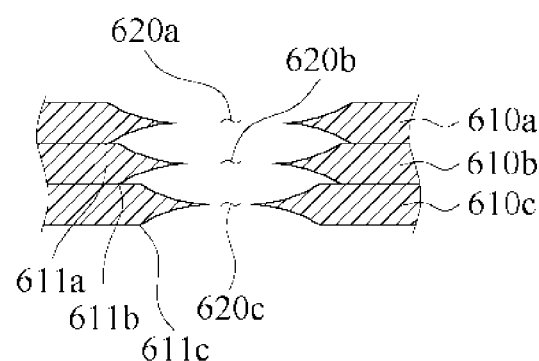
FIG. 14 is a cross-sectional view taken along a line 14-14 of FIG. 13.

FIG. 13 is a top view illustrating another example of a plurality of laminated screens according to an example embodiment, and FIG. 14 is a cross-sectional view taken along a line 14-14 of FIG. 13.

Referring to FIGS. 13 and 14, a device 6 for reducing a size of a biological tissue may include a plurality of screens 60a, 60b, and 60c laminated in sequence. The plurality of screens 60a, 60b, and 60c may respectively include plates 610a, 610b, and 610c and through holes 620a, 620b, and 620c defined by a plurality of edges 611a, a plurality of edges 611b, and a plurality of edges 611c. As described with reference to FIG. 10, each of the plurality of edges 611a, 611b, and may have a plurality of extension portions on both sides based on a tip.

In the example embodiment, the through holes 620a, 620b, and 620c of the plurality of screens 60a, 60b, and 60c laminated in sequence (from top to bottom as shown in FIG. 14) may overlap one another in a direction in which sizes thereof decrease.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

The invention claimed is:

1. A device for reducing a size of a biological tissue, the device comprising:
a front cover including an inlet port through which the biological tissue flows;
a rear cover coupled to the front cover, and including an outlet port through which the biological tissue flows;
a passage connecting the inlet port and the outlet port between the front cover and the rear cover; and
a screen configured to reduce the size of the biological tissue, wherein the screen is accepted between the front cover and the rear cover such that the biological tissue flows inside the front cover via the inlet port, passes the screen along the passage, and then flows from inside to outside the rear cover via the outlet port, wherein the screen includes:
a plate having a first and second sides; and
a through hole formed through the plate, the through hole being defined by a plurality of edges penetrating the first and second sides; and
a protrusion that protrudes toward a central portion of the through hole from the plurality of edges in a plane which is the same as a plane of the plate and is parallel to the plate,
wherein while the biological tissue passes through the through hole, the plurality of edges of the through hole and the protrusion that the plurality of edges define are configured to scratch or tear the biological tissue by applying a pressure on the biological tissue such that a size of the biological tissue decreases.

2. The device of claim 1, wherein a width of the protrusion decreases toward the central portion of the through hole such that a tip is formed.

3. The device of claim 1, wherein the through hole comprises linear portions formed on both sides based on the protrusion that the plurality of edges define.

4. The device of claim 1, wherein the through hole comprises:
an extension portion configured to extend from each of the plurality of edges toward the central portion of the through hole defined by the plurality of edges; and
a tip formed at an end of the extension portion and configured to scratch and tear the biological tissue.

5. The device of claim 4, wherein the through hole further comprises:
an additional extension portion formed on a side opposite to the extension portion based on the tip and configured to extend toward the central portion of the through hole defined by the plurality of edges.

6. The device of claim 1, wherein a protruding direction of the protrusion is not parallel to a moving direction of the biological tissue passing through the through hole.

7. A device for reducing a size of a biological tissue, the device comprising:
a first screen comprising a first plate, a first set of through holes defined by a plurality of first edges of the first plate and penetrating a front and a rear of the first plate, and a first set of protrusions protruding toward a central portion of each of the first set of through holes in a plane which is the same as a plane of the first plate and being parallel to the first plate; and
a second screen comprising a second plate laminated to the first plate, a second set of through holes defined by a plurality of second edges of the second plate and penetrating a front and a rear of the second plate, and a set of protrusion protrusions that protrude toward a central portion of each of the second set of through holes in a plane which is the same as a plane of the second plate and being parallel to the second plate, wherein each through hole of the first set of through hole holes is axially aligned with one of the through holes of the second set of through holes and is larger in size than the one of the second through holes of the second set of through holes with which it is aligned.

8. The device of claim 7, wherein protruding directions of the first protrusion and the second protrusion are not parallel to a moving direction of the biological tissue sequentially passing through the first through hole and the second through hole.

9. A device for reducing a size of a biological tissue, the device comprising:
- a plate having first and second sides; and
- a through hole formed through the plate, the through hole being defined by a plurality of edges penetrating the first and second sides and comprising a first group of protrusions and a second group of protrusions, wherein the first group of protrusions protrude from the first side of the plate while forming an angle with respect to the plate, and the second group of protrusions protrude from the second side of the plate while forming an angle with respect to the plate,
- wherein while the biological tissue passes through the through hole, the plurality of edges and the first group of protrusions and second group of protrusions that the plurality of edges define are configured to scratch or tear the biological tissue by applying a pressure on the biological tissue.

10. The device of claim 9, wherein a width of each protrusion in the first group of protrusions and second group of protrusions decreases toward the central portion of the through hole such that a tip is formed.

11. The device of claim 9, wherein the through hole comprises linear portions formed on both sides based on the first group of protrusions and second group of protrusions that the plurality of edges define.

12. The device of claim 9, wherein the through hole comprises:
- an extension portion configured to extend from each of the plurality of edges toward the central portion of the through hole defined by the plurality of edges; and
- a tip formed at an end of the extension portion and configured to scratch and tear the biological tissue.

13. The device of claim 12, wherein the through hole further comprises:
- an additional extension portion formed on a side opposite to the extension portion based on the tip and configured to extend toward the central portion of the through hole defined by the plurality of edges.

14. The device of claim 9, wherein a protruding direction of the first group protrusions and second group of protrusions is not parallel to a moving direction of the biological tissue passing through the through hole.

* * * * *